United States Patent [19]

Thomas et al.

[11] Patent Number: 4,769,369
[45] Date of Patent: * Sep. 6, 1988

[54] ANTI-ALLERGY 1(2H)-PHTHALAZINONES

[75] Inventors: Telfer L. Thomas, Pittsford; Lesley A. Radov, Penfield, both of N.Y.

[73] Assignee: Pennwalt Corporation, Philadelphia, Pa.

[ * ] Notice: The portion of the term of this patent subsequent to May 12, 2004 has been disclaimed.

[21] Appl. No.: 931,279

[22] Filed: Nov. 14, 1986

[51] Int. Cl.$^4$ .................. C07D 237/32; C07D 401/12; C07D 403/12; A61K 31/50

[52] U.S. Cl. ............................. 514/234.5; 514/248; 544/237; 544/116

[58] Field of Search ............... 544/237, 116; 514/222, 514/232, 234, 248

[56] References Cited

U.S. PATENT DOCUMENTS 4,665,181  5/1987  Thomas et al. ................. 544/237

FOREIGN PATENT DOCUMENTS 2632656  2/1977  Fed. Rep. of Germany .

*Primary Examiner*—Mark L. Berch

[57] ABSTRACT

Novel 1 2(H)-phthalazones are disclosed along with a method of treating either allergic rihinitis or bronchial asthma by the administration to a mammal an effective amount of a compound of the formula:

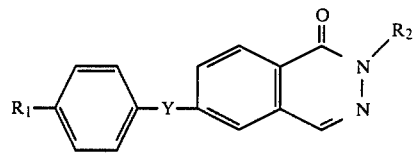

wherein
$R_1$ is hydrogen, hydroxyl, $C_1$–$C_4$ alkoxy, or $C_1$–$C_4$ alkylthio,
$R_2$ is

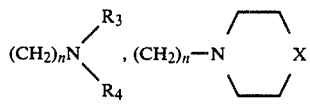

or 1-pyrrolidinyl,
$R_3$ and $R_4$ are independently hydrogen or $C_1$–$C_4$ alkyl,
X is $CH_2$, O or $NR_5$,
Y is ethylene or ethenylene,
$R_5$ is hydrogen or $C_1$–$C_4$ alkyl,
n is 2, 3 or 4,
and all stereoisomeric forms and pharmaceutical acceptable addition salts thereof.

14 Claims, No Drawings

ANTI-ALLERGY 1(2H)-PHTHALAZINONES

BACKGROUND OF THE INVENTION

Allergic rhinitis (e.g., hayfever) and bronchial asthma can result from the inhalation of specific antigenic materials (allergens) by susceptible individuals who respond with Immunoglobulin E (IgE)-mediated reactions. The interaction of the allergen with the IgE molecule, on the surface of a mast cell, leads to the release of a variety of bio-chemical mediators presumed to be responsible for symptoms such as vasodilation, edema, increased mucus secretion, cellular recruitment and increased capillary permeability. In addition to histamine, other mediators, such as the sulfidopeptide leukotrienes $LTC_4$ and $LTD_4$, are likely to be involved in the manifestation of many of these symptoms.

Drugs which are useful in the treatment of the above-mentioned allergic responses are believed to exert their effects by inhibiting mast cell mediator release, either by blocking the effects of these mediators on their targer cell or by relaxing airway smooth muscle. Compounds that either inhibit $LTC_4$ induced contractions of the guinea pig ileum, inhibit edema in the rat anaphalaxis test, or inhibit the wheal reaction in the rat alergic mediator induced thermal vascular permeability test, are expected to be useful in the treatment of bronchial asthma and allergic rhinitis.

SUMMARY OF THE INVENTION

The present invention is, in part, a compound of the formula I,

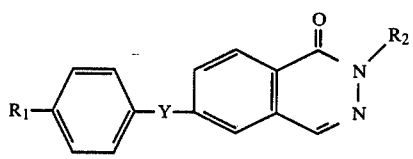

wherein
$R_1$ is hydrogen, hydroxyl, $C_1-C_4$ alkoxy, or $C_1-C_4$ alkylthio,
$R_2$ is

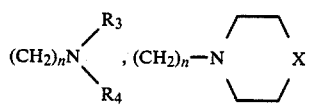

or 1-pyrrolidinyl,
$R_3$ and $R_4$ are independently hydrogen or $C_1-C_4$ alkyl,
X is $CH_2$, O or $NR_5$,
Y is ethylene or ethenylene,
$R_5$ is hydrogen or $C_1-C_4$ alkyl, and
n is 2, 3 or 4,
and all stereoisomeric forms and pharmaceutically acceptable addition salts thereof, provided that either
(1) $R_1$ is $C_1-C_4$ alkylthio;
(2) X is O or $NR_5$; or
(3) $R_1$ is $C_1-C_4$ alkylthio and X is O or $NR_5$.

In a subgeneric aspect, the invention is a compound of formula I as defined in the preceding paragraph, but $R_1$ is limited to hydroxyl, $C_1-C_4$ alkoxy or $C_1-C_4$ alkylthio.

The invention is, in part, the following novel 1(2H)-phthalazinones:
trans-6-[2-(4-methoxyphenyl)ethenyl]-2-[2-(diisopropylamino)ethyl]phthalazin-1(2H)-one hydrobromide,
trans-6-[2-(4-methoxyphenyl)ethenyl]-2-(3-piperidinopropyl)phthalazin-1(2H)-one hydrobromide,
trans-6-[2-(4-methoxyphenyl)ethenyl]-2-[3-(methylamino)propyl]-phthalazin-1(2H)-one hydrobromide,
trans-6-[2-(4-methoxyphenyl)ethenyl]-2-[2-(dimethylamino)-ethyl]-phthalazin-1(2H)-one hydrobromide,
trans-6-[2-(4-methoxyphenyl)ethenyl]-2-(3-aminopropyl)phthalazin-1(2H)-one hydrobromide,
trans-6-[2-(4-methoxyphenyl)ethenyl]-2-[4-(dimethylamino)butyl]-phthalazin-1(2H)-one bromide, and
cis-6-[2-(4-methoxyphenyl)ethenyl]-2-[3-(dimethylamino)propyl]-phthalazin-1(2H)-one cyclohexylsulfamate.

The invention is also, in part, a method of treating either allergic rhinitis or bronchial asthma which comprises the administration to a mammal in need of such treatment of an effective amount of a compound of the formula I,

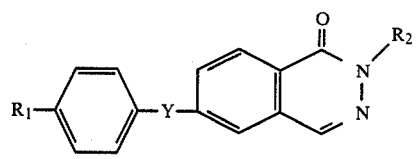

wherein
$R_1$ is hydrogen, hydroxyl, $C_1-C_4$ alkoxy, or $C_1-C_4$ alkylthio,
$R_2$ is

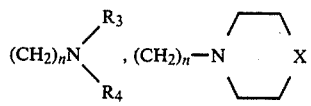

or 1-pyrrolidinyl,
$R_3$ and $R_4$ are independently hydrogen or $C_1-C_4$ alkyl,
X is $CH_2$, O or $NR_5$,
Y is ethylene or ethenylene,
$R_5$ is hydrogen or $C_1-C_4$ alkyl,
n is 2, 3 or 4,
and all stereoisomeric forms and pharmaceutically acceptable addition salts thereof. These compounds of the formula I inhibit $LTC_4$-induced contractions of the guinea pig ileum [in a test described below], inhibit edema in the rat anaphalaxis test described below and inhibit the wheal reaction in a rat allergic mediator induced dermal vascular permeability test described below. As a result, these compounds of formula I are expected to be useful in the treatment of bronchial asthma and allergic rhinitis in mammals, including humans.

In a subgeneric aspect, the invention is a method as defined in the preceding paragraph, but $R_1$ is limited to hydroxyl, $C_1-C_4$ alkoxy, or $C_1-C_4$ alkylthio.

The preferred 1(2H)-phthalazinones of formula I are those wherein,
$R_1$ is methoxy, and R$_2$ is 3-(dimethylamino)propyl, 2-(dimethylamino)ethyl, 4-(dimethylamino)butyl, 3-piperidinopropyl, or 3-morpholinopropyl and the stereoisomeric form is the trans isomer.

The preferred salts are acid addition salts of inorganic acids such as hydrogen chloride, hydrogen bromide, sulfuric acid, or organic acids such as acetic, lactic, maleic, fumaric, malic, succinic, tartaric and methanesulfonic acids.

Methods of Preparation

Methods for preparing compounds of Formula I and appropriate intermediates are disclosed in U.S. patent application Ser. No. 611,310, filed on May 17, 1984, U.S. Pat. No. 4,665,181 (named inventors were Telfer Lawson Thomas and Leslie Ann Radov) which application is incorporated by reference here. In addition, an alternative route to the compounds of Formula I is shown in Scheme I.

Scheme I

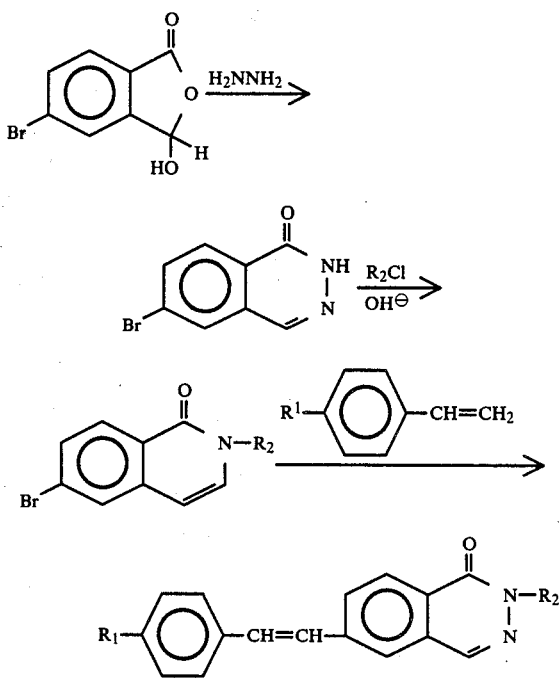

5-Bromo-3-hydroxyphthalide is reacted in alcoholic solution with hydrazine to give 6-bromophthalazin-1(2H)-one which in turn is reacted with the appropriate (dialkylamino)alkylhalide in a polar solvent such as DMSO in the presence of a base such as KOH to give the 2-(dialkylaminoalkyl)-6-bromophthalazin-1(2H)-one. The styryl group is then attached by reacting the 6-bromo-2-substituted-phthalazin-1(2H)-one with styrene or 4-methoxystyrene in solvents such as DMSO or acetonitrile or mixtures thereof, in the presence of the reagents tri(o-tolyl)phosphine and palladium acetate to give the 6-[2-(phenyl or 4-methoxyphenyl)ethenyl]-2-[(dialkylamino)-alkyl]phthalazin-1(2H)-one. Specific methods for preparing the compounds of this invention are disclosed in the examples.

Formulations

For pharmaceutical purposes, the compounds of this invention can be administered to warm-blooded animals perorally or parenterally as active ingredients in customary dosage unit compositions. These compositions consist essentially of a dosage unit form containing the active ingredient and at least one inert pharmaceutical carrier. Dosage unit forms contemplated by the present invention include tablets, capsules, solutions, suspensions, lozenges, coated pills and parenteral compositions such as intramuscular, intravenous or intradermal preparations. Sustained release dosage forms are also contemplated where the active ingredient is bound to an ion exchange resin which, optionally, can be coated with a diffusion barrier coating to mdify the release properties of the resin.

The quantity of active ingredient administered in such dosage forms can vary over a wide range depending upon the mode of administration, the size and weight of the patient and whether the nature of the treatment is prophylactic or therapeutic in nature. In general dosage unit forms contain from about 5 mg to 100 mg of the active ingredient and in man the dose is administered from 1 to 4 times daily. The total daily dosage will be from about 5 mg to 500 mg although lower and higher amounts can be used. A preferred total daily dose would be from 10 mg to 100 mg of active ingredient. p Guinea Pig Ileum Test The methodology for determining the degree of inhibition of LTC$_4$ induced contractions of the guinea pig ileum by the compounds of formula 1 is described below and the results, expressed as the micromolar concentration required to inhibit the contraction by 50 percent, are given in Table I.

Four replicate, small pieces of guinea pig ileum were suspended in Kreb's physiological salt solution in a 10 ml tissue bath to a gram tension of approximately 1.0. These pieces of tissue were then chemically stimulated with 6 microliters of purified leukotriene C$_4$ (LTC$_4$) yielding a final concentration in the bath of 6 nanomoles. Responses (tissue contraction) were measured isometrically using a Harvard transducer and a Beckman recorder. Upon addition of the LTC$_4$, the tissue was allowed to sit for approximately 15–30 minutes to reach maximal stimulation. The test compound dissolved in a maximum volume of 100 microliters of either saline, dimethylsulfoxide or ethanol was then added to the tissue preparation and the change in gram tension was recorded.

TABLE 1

| Inhibition of LTC$_4$-Induced Guinea Pig Smooth Muscle Contractions | |
|---|---|
| Test Compound-Title Compound of Example No.: | IC$_{50}$ ($\mu$m): |
| II | 3.4 |
| III | 16.6 |
| IV | 0.1 |
| VI | 16.8 |
| IX | 10 |
| X | 10.5 |
| XI | 10 |
| XII | 13.6 |
| XIV | 31.6 |

Rat Anaphylaxis Test

In the rat anaphylaxis test, groups consisting of 15–20 rats are intraperitoneally sensitized on day zero with 500 $\mu$g of bovine serum albumin-absorbed alum admixed with 2×10$^{10}$ killed Bordatella pertussis vaccine organisms. Fourteen days later, the test compound suspended in 0.5 to 1.0 ml of 1% Cleargel or saline (0.85% NaCl in H$_2$O) is administered ip or po and, one hour later, the right hind paw is injected subcutaneously with 100 μg of bovine serum albumin dissolved in 0.1 ml of saline. The paw volume is measured using a mercury plethysmometer prior to drug administration and 90 minutes post antigenic challenge. The present inhibition of edema is calculated as the difference in volume between the control and drug treated groups, divided by the control volume, and then multiplied times 100. The positive control drug, theophylline (90 mg/kg, po) is included in each assay. Statistical analysis of the data is done using an analysis of variance program. See Tables 2 and 3 for results obtained with this test.

In Tables 2 and 3, and elsewhere in this application, PR 948-257C stands for trans-6-[2-(4-methoxyphenyl)ethenyl]-2-[3-(dimethylamino)propyl]-phthalazin-1(2H)-one hydrobromide.

TABLE 2

Effect of Intraperitoneal Administration of PR 948-257C on the Active Anaphylaxis Response in Male, Sprague Dawley Rats[a]

| Group | N | Dose (mg/kg) | Paw Volume[c] Mean ± S.E. | % Inhibition |
|---|---|---|---|---|
| Vehicle | 20 | — | 3.8 ± 2.3 | — |
| Theophylline[b] | 17 | 90 | 0.9 ± 0.7* | 76 |
| PR 948-257 | 20 | 100 | 0.4 ± 0.8* | 91 |
|  | 20 | 75 | 0.7 ± 0.8* | 83 |
|  | 20 | 50 | 1.7 ± 1.3* | 56 |
| Vehicle | 20 | — | 4.3 ± 2.6 | — |
| Theophylline[b] | 20 | 90 | 0.4 ± 0.6* | 92 |
| PR 948-257 | 20 | 25 | 1.9 ± 1.4* | 55 |
|  | 20 | 12.5 | 2.1 ± 1.8* | 52 |
|  | 20 | 6.25 | 2.2 ± 1.9* | 48 |
| Vehicle | 20 | — | 4.3 ± 2.3 | — |
| Theophylline[b] | 29 | 90 | 0.5 ± 0.5* | 87 |
| PR 948-257 | 19 | 6 | 3.7 ± 2.6 | 12 |
|  | 19 | 4 | 4.9 ± 2.3 | +14 |
|  | 20 | 2.5 | 4.7 ± 2.8 | +11 |

[a]The animals were intraperitoneally sensitized with 500 ug of bovine serum albumin (BSA) 14 days prior to an intraplantar paw challenge with 100 ug of BSA. The test compounds were administered one hour prior to the BSA challenge.
[b]Theophylline was orally administered.
[c]The change in paw volume is recorded as the difference between the left uninjected and right uninjected paw volume of the same animal.
*Statistically significant decrease from control values; $p < .05$, using the analysis of variance test.

TABLE 3

The Effect of Oral Administration of PR 948-257C on the Active Anaphylaxis Response of Male, Sprague Dawley Rats[a]

| Group | N | Dose (mg/kg) | Paw Volume ± S.E. mm of Hg[b] | % Inhibition |
|---|---|---|---|---|
| Saline | 20 | — | 3.60 ± .6 | — |
| Theophylline | 20 | 90 | 0.65 ± .2* | 82 |
| PR 948-257C | 20 | 100 | 1.65 ± .36* | 54 |
|  | 19 | 75 | 2.26 ± .32 | 37 |
|  | 20 | 50 | 3.10 ± .55 | 14 |

[a]The animals were intraperitoneally sensitized with 500 ug of bovine serum albumin (BSA) 14 days prior to an intraplantar paw challenge with 100 ug of BSA. The test compounds were administered one hour prior to the BSA challenge.
[b]The change in paw volume is recorded as the difference between the left uninjected and right injected paw volume of the same animal.
*Statistically significant decrease from control values; $p \leq .01$ using the analysis of variance test.

Rat Allergic Mediator Induced Dermal Vascular Permeability Test

In this test, groups of ten male rats are intraperitoneally or perorally administered 0.5 ml to 1.0 ml saline solution of either the test compound or positive reference standard cyproheptadine (1 mg/kg) one hour prior to an intravenous injection of 1 ml of a 0.5% solution of Evan's blue dye into naive animals. Ten minutes later, the animals are challenged by intradermally injecting 0.1 ml of a water solution of either serotonin (1 μg/ml), histamine (20 μg/ml) or bradykinin (10 μg/ml) into separate sites on the back. Five minutes following challenge the animals are killed, the skin retracted, and the mean diameter of the blue wheal and flare reaction is calculated as the difference in mean diameter between a saline control and the drug treated group, divided by the control diameter, and then multiplied times 100. Statistical analysis of the data is done using a Student T-test program. See Tables 4 (ip administration of test compound) and 5 (po administration of test compound) for results obtained with the rat allergic mediator induced dermal vascular permeability test. (Set: Serotonin; His: histamine; Bk: bradykinin)

TABLE 4

| Compound | N | Dose (mg/kg) | Wheal Measurement (mm) and Standard Errors | | | % Inhibition | | |
|---|---|---|---|---|---|---|---|---|
| | | | Ser | His | Bk | Ser | His | Bk |
| Control | 10 | — | 11.1 ± 0.2 | 11.2 ± 0.2 | 10.9 ± 0.2 | — | — | — |
| Cyproheptadine | 10 | 1 | 2.8 ± 0.9*** | 0.8 ± 0.8*** | 4.3 ± 4.0*** | 74.8 | 92.9 | 60.6 |
| PR 948 257C | 10 | 50 | 3.5 ± 1.1*** | 2.7 ± 1.1*** | 2.8 ± 1.1*** | 68.5 | 75.9 | 74.3 |
| PR 948-257C | 10 | 25 | 5.4 ± 1.0*** | 5.6 ± 1.0*** | 5.7 ± 1.1*** | 51.4 | 50.0 | 47.7 |
| PR 948-257C | 10 | 12.5 | 8.2 ± 1.0** | 8.2 ± 1.0** | 7.4 ± 1.0*** | 26.1 | 26.8 | 32.1 |

*$p < 0.05$
**$p < 0.01$
***$p < 0.001$

TABLE 5

| Compound | N | Dose (mg/kg) | Wheal Measurement (mm) and Standard Errors | | | % Inhibition | | |
|---|---|---|---|---|---|---|---|---|
| | | | Ser | His | Bk | Ser | His | Bk |
| Control | 10 | — | 10.3 ± 0.4 | 10 ± 0.3 | 9.1 ± 0.3 | — | — | — |
| Cyproheptadine | 10 | 1 | 0.5 ± 0.5*** | 0 ± 0*** | 1.2 ± 0.8*** | 95.1 | 100 | 86.8 |
| PR 948-257C | 10 | 12.5 | 7.9 ± 0.4*** | 8.3 ± 0.3*** | 8.0 ± 0.4* | 23.3 | 17 | 12.1 |
| PR 948-257C | 10 | 25 | 5.9 ± 0.7*** | 4.3 ± 1.0*** | 4.7 ± 0.8*** | 42.7 | 57 | 48.4 |

TABLE 5-continued

| Compound | N | Dose (mg/kg) | Wheal Measurement (mm) and Standard Errors | | | % Inhibition | | |
|---|---|---|---|---|---|---|---|---|
| | | | Ser | His | Bk | Ser | His | Bk |
| PR 948-257C | 10 | 50 | 4.0 ± 1.1*** | 2.9 ± 1.2*** | 3.3 ± 1.1*** | 61.1 | 71 | 63.8 |

*$p < 0.05$
**$p < 0.01$
***$p < 0.001$

EXAMPLES

Example I

Trans-6-[2-(4-methoxyphenyl)ethenyl]-2-[2-(diisopropylamino)-ethyl]phthalazin-1(2H)-one hydrobromide

Step a

6-Bromophthalazin-1(2H)-one

5-Bromo-3-hydroxyphthalide (49 gm) was slurred in 200 ml isopropanol. Hydrazine (20 ml) was added and the mixture refluxed for 2 hours. The reaction mixture was allowed to cool and the product filtered off, washed with isopropanol and dried. The product weighed 46.8 gm and melted at 280°–283° C.

Step b

6-Bromo-2-[2-(diisopropylamino)ethyl]phthalazin-1(2H)-one

6-Bromophthalazinone (11.2 gm, 0.05 mole) was slurried in 80 ml dimethylsulfoxide. To this was added 22 ml 45% KOH (0.25 mole). After stirring 10 minutes 16 gm 2-(diisopropylamino)ethyl chloride hydrochloride was added and the mixture stirred for 18 hours. A water bath was used to moderate the slightly exothermic reaction (temperature $< = 25°$). Water (100 ml) was added to the reaction mixture, which was then stirred another hour.

The product was filtered, washed to colorless washings with water and dried. The product weighed=17.7 gm. Tlc (40% ethyl acetate in cyclohexane on an ammonia treated silica plate) showed a single product $R_f=0.59$; no starting material, $R_f=0.23$, was visible. Two barely visible trace spots, $R_f=0.36$ and 0.32 were also present.

Recrystallization of a 6.3 gm sample from 35 ml methoxyethanol yielded 3.8 gm of product showing a single spot on tlc.

Step c

Trans-6-[2-(4-methoxyphenyl)ethenyl]-2-[2-(diisopropylamino)ethyl]phthalazin-1(2H)-one hydrobromide 6-Bromo-2-[2-(diisopropylamino)ethyl]phthalazin-1(2H)-one (10.6 gm, 0.03 mole, prepared in Example I) was stirred into 16 ml DMSO plus 16 ml acetonitrile. To the resulting mixture was added 4.5 gm 4-methoxystyrene (0.033 mole), 0.1 gm tri(o-tolyl)phosphine, and 0.02 gm palladium acetate. The reaction mixture was stirred at reflux (95°–100° C.) for 24 hours. Allowed to cool to about 60° C. and diluted with 60 ml of isopropanol. Stirred for an hour, filtered, washed to colorless washings with isopropanol and dried. The product weighed 11.3 gm. After recrystallization from 80 ml 1:1:ethanol:-water the product weighed 10.0 gm and melted at 251°–252° C.

EXAMPLE II

Trans-6-[2-(4-methoxyphenyl)ethenyl]-2-(3-piperidinopropyl)phthalazin-1(2H)-one hydrobromide 6-Bromo-2-(3-piperidinopropyl)phthalazin-1(2H)-one (7.2 gm, 0.018 mole) (prepared as in Example I, except that 1-(3-chloropropyl)piperidine hydrochloride was substituted for the 2-(diisopropylamino)ethyl chloride hydrochloride) was stirred into 10 ml DMSO plus 10 ml acetonitrile. To the resulting mixture was added 2.8 gm 4-methoxystyrene (0.021 mole), 0.1 gm tri(o-tolyl)phosphine, and 0.02 gm palladium acetate. The reaction mixture was stirred at reflux (95°–100° C.) for 24 hours. Allowed to cool to about 60° C. and diluted with 40 ml of isopropanol. Stirred for an hour, filtered, washed to colorless washings with isopropanol and dried. The product weighed 8.6 gm. After recrystallization from 50 ml methoxyethanol the product weighed 6.4 gm and melted at 248°–250° C.

Example III

Trans-6-[2-(4-methoxyphenyl)ethenyl]-2-[2-(dimethylamino)ethyl]-phthalazin-1(2H)-one hydrobromide 6-Bromo-2-[2-(dimethyamino)ethyl]phthalazin-1(2H)-one (7.2 gm, 0.018 mole) (prepared as in Example I, except that 2-(dimethylamino)ethyl chloride hydrochloride was substituted for the 2-(diisopropylamino)ethyl chloride hydrochloride) was stirred into 16 ml DMSO plus 16 ml acetonitrile. To the resulting mixture was added 4.5 gm 4-methoxystyrene (0.033 mole), 0.1 gm tri(o-tolyl)phosphine, and 0.02 gm palladium acetate. The reaction mixture was stirred at reflux (95°–100° C.) for 24 hours. Allowed to cool to about 60° C. and diluted with 60 ml of isopropanol. Stirred for an hour, filtered, washed to colorless washings with isopropanol and dried. The product weighed 10.7 gm. After recrystallization from 240 ml methoxyethanol the product weighed 6.4 gm and melted at 265°–267° C.

Example IV

Trans-6-[2-(4-methoxyphenyl)ethenyl]-2-(2-morpholinoethyl)phthalazin-1(2H)-one hydrobromide 6-Bromo-2-(2-morpholinoethyl)phthalazin-1(2H)-one (10.1 gm, 0.03 mole) (prepared as in Example I, except that 2-morpholinoethyl chloride hydrochloride was substituted for the 2-(diisopropylamino)ethyl chloride hydrochloride) was stirred into 16 ml DMSO plus 16 ml acetonitrile. To the resulting mixture was added 4.5 gm 4-methoxystyrene (0.033 mole), 0.1 gm tri(o-tolyl)phosphine, and 0.02 gm palladium acetate. The reaction mixture was stirred at reflux (95°–100° C.) for 24 hours. Allowed to cool to about 60° C. and diluted with 60 ml of isopropanol. Stirred for an hour, filtered, washed to colorless washings with isopropanol and dried. The product weighed 11.9 gm. After recrystallization from 40 ml ethanol plus 30 ml water the product weighed 9.2 gm and melted at 254°–256° C.

Example V

Trans-6-[2-(4-methoxyphenyl)ethenyl]-2-[3-(1-piperazino)propyl]phthalazin-1(2H)-one 6-Bromo-2-(3-piperazinopropyl)phthalazin-1(2H)-one (2.1 gm, 0.0062 mole) (prepared as in Example I, except that 3-piperazinopropyl chloride hydrochloride was substituted for the 2-(diisopropylamino)ethyl chloride hydrochloride) was stirred into 4 ml DMSO plus 4 ml acetonitrile. To the resulting mixture was added 1 gm 4-methoxystyrene (0.0075 mole), 0.05 gm tri(o-tolyl)phosphine, and 0.01 gm palladium acetate. The reaction mixture was stirred at reflux (95°–100° C.) for 24 hours. Allowed to cool to about 60° C. and diluted with 20 ml of isopropanol. Stirred for 2 hours, filtered, washed to colorless washings with isopropanol and dried. The product weighed 1.4 gm. and melted at 206°–209° C.

Example VI

6-[2-(4-methoxyphenyl)ethyl]-2-[3-(dimethylamino)propyl]phthalazin-1(2H)-one

6-[2-(4-methoxyphenyl)ethenyl]-2-[3-(dimethylamino)propyl]phthalazin-1(2H)-one (9 gm) was dissolved in 200 ml methoxyethanol and reduced on a Parr hydrogenator using 1 gm of 10% palladium on carbon as catalyst. Reduction was complete within 2 hours. The catalyst was filtered off, the solvent removed on a rotary evaporator and the residue recrystallized from 500 ml of isoproanol. The product weighed 8.3 gm and melted at 201°–203° C.

Example VII

Trans-6[2-(4-methoxyphenyl)ethenyl]-2-[3-(methylamino)propyl]phthalazin-1(2H)-one hydrobromide Trans-6-[2-(4-Methoxyphenyl)ethenyl]-2-[3-(dimethylamino)propyl]phthalazin-1(2H)-one (8.9 gm, 0.024 mole) in 150 ml toluene was treated with 27 ml 12% phosgene in toluene and stirred for 7 days. The solvent was removed and the residue recrystallized from 25 ml carbon tetrachloride plus 15 ml toluene, yielding 5.4 gm of the chlorocarbonyl intermediate.

This intermediate was heated in 125 ml water at about 90° C. for 30 minutes. The solution was clarified, basified with potassium carbonate and extracted into ethyl acetate. The solvent was removed and the residue dissolved in 30 ml ethanol and acidified with 3 ml 30% HBr in acetic acid. The product was allowed to crystallize, filtered and washed with isopropanol. The purified product weighed 3.8 gm and melted at 256°–258° C.

Example VIII

Trans-6-[2-(4-methoxyphenyl)ethenyl]-2-(3-aminopropyl)phthalazin-1(2H)-one hydrobromide Step a 6-Bromo-2-(3-carboxypropyl)phthalazin-1(2H)-one To a slurry of 56 gm 6-bromophthalazin-1(2H)-one (0.25 mole) in 600 ml DMSO was added 110 ml 45% KOH followed by 58.5 gm ethyl 4-bromobutyrate. The temperature of the mildly exothermic reaction was moderated with a water bath (ca. 25° C.) and was stirred for 20 hours. Ethanol (750 ml) was added, then the mixture was acidified with 125 ml concentrated HCl, diluted with 2500 ml water over about 30 minutes, stirred an additional 30 minutes, filtered, washed with water and isopropanol and dried. The product weighed 63.6 gm. A tlc of the product showed product, $R_f=0.43$ plus a trace of starting material, $R_f=0.63$.

Step b

6-Bromo-2-(3-aminopropyl)phthalazin-1(2H)-one

6-Bromo-2-(3-carboxypropyl)phthalazin-1(2H)-one (9.3 gm, 0.03 mole, prepared in Example XIV) was dissolved in 185 ml acetone by adding 4.7 ml triethylamine (0.0335 mole). The slightly cloudy solution was clarified, cooled to <10° C. and 3.8 gm methyl chloroformate (0.04 mole) was added over about 5 minutes. Stirred with cooling for another 30 minutes, then added a solution of 4 gm sodium azide (0.062 mole) in 25 ml water. Stirred for 30 minutes, added to 400 ml ice water and extracted three times with 80 ml methylene dichloride. This solution was dried, 4 ml of trifluoroacetic acid was added, and the solution refluxed for 18 hours. Methanol (100 ml) was added and the solution shaken with dilute potassium carbonate solution to free the base. The resulting solution was acidified with 10 ml of 30% HBr in acetic acid, diluted with 900 ml ether, filtered and washed with ethyl acetate. The product weighed 6.3 gm and showed a single spot on tlc, $R_f=0.28$ (using 10% methanol in chloroform on an ammonia treated silica plate).

Step c

6-Bromo-2-[3-[(t-butoxycarbonyl)amino)propyl]phthalazin-1(2H)-one

6-Bromo-2-(3-aminopropyl)phthalazin-1(2H)-one (13.6 gm, prepared as in Example XV) was dissolved in a mixture of 130 ml chloroform and 60 ml t-butanol. Triethylamine (5.8 ml) and 9.1 gm of di(t-butyl)dicarbonate were added and the solution was allowed to stand for 5 days in the dark. The solution was added to a solution of 15 gm citric acid in 380 ml water and stirred for a few minutes. The chloroform layer was separated and the aqueous layer extracted twice more with 75 ml chloroform. The combined chloroform extracts were extracted twice with 75 ml water and once with 75 ml potassium carbonate solution. The solution was dried, the solvent removed and the residue slurried in 110 ml of cyclohexane for 1 hour. The product was filtered off and washed with cyclohexane. It weighed 12.7 gm and melted at 130°–132° C.

Step d

Trans-6-[2-(4-methoxyphenyl)ethenyl]-2-[3-aminopropyl]phthalazin-1(2H)-one hydrobromide A mixture of 9.1 gm 6-Bromo-2-[3-[(t-butoxycarbonyl)amino]propyl]phthalazin-1(2H)-one (0.0238 mole, prepared as described above), 3.7 ml 4-methoxystyrene (0.028 mole), 18 ml DMSO, 18 ml acetonitrile, 3 gm triethylamine (0.03 mole), 0.15 gm tri-(o-tolyl)phosphine (0.0005 mole) and 0.03 gm palladium acetate (0.00013 mole) were refluxed together for 20 hours. It was diluted with 40 ml isopropanol after allowing to cool to about 80° C. The solution was added to 200 ml water and 200 ml ethyl acetate shaken well, and the organic layer separated. The water layer was extracted twice more with 100 ml ethyl acetate, the organic solution washed with water, dried and concentrated to dryness. The crude product (weight=9.3 gm) was recrystallized from 45 ml isopropanol, yielding 6.6 gm of pure product having an $R_f$ of 0.26 using 40% ethyl acetate in cyclohexane on a silica plate.

The protecting group was removed by slurrying in 130 ml isopropanol containing 160 ml 30% HBr in acetic acid. The product was filtered off and washed with isopropanol. It weighed 5.1 gm and showed a single spot on tlc. After recrystallization from 65 ml 95% ethanol plus 10 ml water it weighed 3.9 gm and melted at 291°-293° C.

Example IX

Trans-6-[2-(4-methoxyphenyl)ethenyl]-2-[4-dimethylamino)butyl]phthalazin-1(2H)-one bromide

Step a

6-Bromo-2-[4-(dimethylamino)butyl]phthalazin-1(2H)-one

6-Bromo-2-(3-carboxypropyl)phthalazin-1(2H)-one (18.4 gm 0.06 mole, prepared as described above) was dissolved in a mixture of 400 ml methylene dichloride and 10 ml triethylamine. Methyl chloroformate (7.6 gm, 0.07 mole) was added, the mixture stirred for a few minutes, then the solvent removed on a rotary evaporator. The residue was dissolved in 30 ml absolute ethanol and 1.2 gm sodium borohydride (0.03 mole) was added portionwise over 1 hour. The mixture was stirred for 20 hours, diluted with 20 ml water, stirred 15 minutes, then basified with 25 ml water containing 5 ml 45% potassium hydroxide and stirred 20 hours. The solution was acidified and the product filtered off, washed with water and dried. The product weighed 7.1 gm. Work up of the filtrates allowed recovery of 9.1 gm of starting acid. bp The alcohol above (7.1 gm, 0.024 mole) was dissolved in 75 ml pyridine and stirred with 8.6 gm p-toluenesulfonyl chloride for 6 hours at ambient temperature. The mixture was added to 225 gm ice plus 125 ml concentrated HCl and the product extracted into methylene dichloride. Removal of the solvent left 7.5 gm solid. This material was dissolved in 45 ml DMSO and 8 ml dimethylamine. After heating at 80° C. for 6 hours the mixture was allowed to cool and stand over night. It was added to 300 ml water and extracted three times with 150 ml ethyl acetate, washing each extract three times with 75 ml water. The product was then extracted from the organic solution with three 100 ml portions of dilute HCl. The acidic solution was basified, the product extracted into chloroform, dried and the solvent removed, leaving 3.1 gm of crystalline product.

Step b

Trans-6-[2-(4-methoxyphenyl)ethenyl]-2-[4-dimethylamino)butyl]phthalazin-1(2H)-one hydrobromide The procedure used was identical to that used in preparing 6-[2-4-methoxyphenyl)ethenyl]-2-[2-(dimethylamino)ethyl]phthalazin-1(2H)-one (Example III above), except that 6-Bromo-2-[4-(dimethylamino)butyl-])phthalazin-1(2H)-one was substituted for 6-Bromo-2-[2-(dimethyamino)ethyl]phthalazin-1(2H)-one. The weight of product obtained from 7.5 gm starting halide was 7.1 gm after recrystallization from 50 ml of methoxyethanol. It melted at 225°-227° C.

Example X

Cis-6-[2-(4-methoxyphenyl)ethenyl]-2-[3-dimethylaminopropyl]phthalazin-1(2H)-one cyclohexylsulfamate Trans-6-[2-(4-methoxyphenyl)ethenyl]-2-[3-dimethylaminopropyl]-phthalazin-1(2H)-one (48 gm) in 7000 ml 20% isopropanol in ethanol was irradiated in a 12 liter flask with a 450 watt Hanovia ultraviolet lamp for 8 hours. The solution was concentrated to dryness and the residue slurried in 55 ml ethanol, heated to a cloudy solution, allowed to cool and filtered off the trans-isomer that had crystallized from the solution. The filtrate, which was cis-isomer contaminated with a little trans-isomer and some minor impurities, was diluted with water, basified and the product extracted into chloroform. The solution was concentrated to dryness and the residue chromatographed on a preparative liquid chromatographic apparatus using a silica column. The product was eluted with a 5:3:1:1 mixture of ethyl acetate:n-butanol:acetic acid:water giving 12.7 gm of oily product. The product was converted to the cyclohexylsulfamic acid salt using 10 gm of the acid in 70 ml of acetone. It weighed 11.6 gm and melted at about 110°-120° C.

Example XI

Trans-6-[2-[4-(methylthio)phenyl]ethenyl]-2-[3-(dimethylamino)propyl]phthalazin-1(2H)-one 6-Bromo-2-[3-(dimethylamino)propyl]phthalazin-1(2H)-one (8.5 gm) (prepared as in Example I, except that 3-(dimethylamino)propyl chloride hydrochloride was substituted for the 2-(diisopropylamino)ethyl chloride hydrochloride) was stirred into 4 ml DMSO plus 4 ml acetonitrile. To the resulting mixture was added 3.7 gm 4-methylthiostyrene, 0.2 gm tri(O-tolyl)phosphine, and 0.04 gm palladium acetate. The reaction mixture was stirred at reflux (95°-100° C.) for 24 hours. The solution was concentrated to dryness on a rotovap and the residue recrystallized from 95% ethanol yielding 5.5 gm of product melting at 210° C.

Example XII

Trans-6-[2-(4-methoxyphenyl)ethenyl]-2-[3-(dimethylamino)propyl]-phthalazin-1(2H)-one hydrobromide The procedure used was identical to that used in preparing 6-[2-(4-methoxyphenyl)ethenyl]-2-[2-(dimethylamino)ethyl]phthalazin-1(2H)-one (Example III above), except that 6-Bromo-2-[3-(dimethylamino)propyl]phthalazin-1(2H)-one was substituted for 6-Bromo-2-[2-(dimethyamino)ethyl]phthalazin-1(2H)-one. The weight of product obtained from 102 gm starting halide was 104 gm after recrystallization from 50 ml of methoxyethanol. It melted at 232°-234° C.

Example XIII

Trans-6-[2-(4-hydroxyphenyl)ethenyl]-2-[3-(dimethylamino)propyl]-phthalazin-1(2H)-one hydrochloride Trans-6-[2-(4-Methoxyphenyl)ethenyl]-2-[3-(dimethylamino)propyl]-phthalazin-1(2H)-one (prepared as in Example XIV) (46.6 gm, 0.122 mole) and 245 gm pyridine hydrochloride were heated together with stirring at 180° C. for 7 hours. The hot melt was added to 1200 ml water and stirred over night. The product was filtered off and washed with three 400 ml portions of water. The damp product was slurried in 350 ml of tetrahydrofuran plus 350 ml methanol, acidified with gaseous HCl, filtered and washed with ethanol. The product, which weighed 36 gm, was recrystallized from 275 ml water. Wgt=30.2 gm, mp=283°–283° C.

Example XIV

Trans-6-[2-(4-Hydroxyphenyl)ethenyl]-2-(2-dimethylaminoethyl)-1(2H)-phthalazinone hydrochloride Following the procedure of Example XIII above trans-6-[2-(4-hydroxyphenyl)ethenyl]-1(2H)phthalazinone (19.8 g) and 2-dimethylaminoethyl chloride hydrochloride (17.3 g) were reacted to give the 2-(2-dimethylaminoethyl) derivative as the hydrochloride (16 g), mp 283°–285° C.

What is claimed is:

1. A compound of the formula

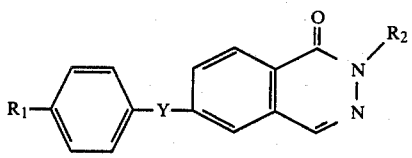

wherein
$R_1$ is hydrogen, hydroxyl, $C_1$-$C_4$ alkoxy, or $C_1$-$C_4$ alkylthio,
$R_2$ is

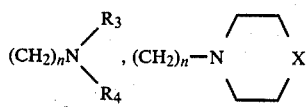

or 1-pyrrolidinyl,
$R_3$ and $R_4$ are independently hydrogen or $C_1$-$C_4$ alkyl,
X is $CH_2$, O or $NR_5$,
Y is ethylene or ethenylene,
$R_5$ is hydrogen or $C_1$-$C_4$ alkyl, and
n is 2, 3 or 4,
and all stereoisomeric forms and pharmaceutically acceptable addition salts thereof, provided that
if $R_1$ is other than $C_1$-$C_4$ alkylthio; then $R_2$ must be either;

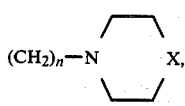

where X is O or $NR_5$, or 1-pyrrolidinyl.

2. A compound as defined in claim 1 provided further that $R_1$ is not hydrogen.

3. Trans-6-[2-(4-methoxyphenyl)ethenyl]-2-[2-diisopropylamino)-ethyl]phthalazin-1(2H)-one and pharmaceutically acceptable salts thereof.

4. Trans-6-[2-(4-methoxyphenyl)ethenyl]-2-(3-piperidinopropyl)-phthalazin-1(2H)-one and pharmaceutically acceptable salts thereof.

5. Trans-6-[2-(4-methoxyphenyl)ethenyl]-2-[3-(methylamino)propyl]-phthalazin-1(2H)-one and pharmaceutically acceptable salts thereof.

6. Trans-6-[2-(4-methoxyphenyl)ethyl)-2-[2-(dimethylamino)ethyl]-phthalazin-1(2H)-one and pharmaceutically acceptable salts thereof.

7. Trans-6-[2-(4-methoxyphenyl)ethenyl]-2-(3-aminopropyl)phthalazin-1(2H)-one and pharmaceutically acceptable salts thereof.

8. Trans-6-[2-(4-methoxyphenyl)ethenyl]-2-[4-dimethylamino)butyl]-phthalazin-1(2H)-one and pharmaceutically acceptable salts thereof.

9. Cis-6-[2-(4-methoxyphenyl)ethenyl]-2-[3-(dimethylaminopropyl]-phthalazin-1(2H)-one and pharmaceutically acceptable salts thereof.

10. The method of treating either allergic rhinitis or bronchial asthma which comprises the administration to a mammal in need of such treatment of an effective amount of a compound of the formula

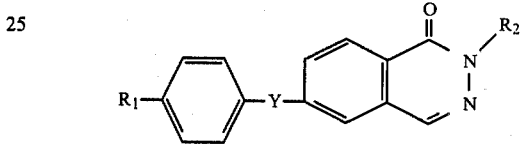

wherein
$R_1$ is hydrogen, hydroxyl, $C_1$-$C_4$ alkoxy, or $C_1$-$C_4$ alkylthio,
$R_2$ is

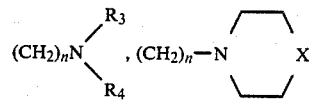

or 1-pyrrolidinyl,
$R_3$ and $R_4$ are independently hydrogen or $C_1$-$C_4$ alkyl,
X is $CH_2$, O or $NR_5$,
Y is ethylene or ethenylene,
$R_5$ is hydrogen or $C_1$-$C_4$ alkyl,
n is 2, 3 or 4,
and all stereoisomeric forms and pharmaceutically acceptable addition salts thereof.

11. The method of claim 10 wherein $R_1$ is hydroxyl, $C_1$-$C_4$ alkylthio.

12. Trans-6-[2-(4-methoxyphenyl)ethenyl]-2-(2morpholinoethyl)-phthalazin-1(2H)-one and pharmaceutically acceptable salts thereof.

13. Trans-6-[2-(4-methoxyphenyl)ethenyl]-2-[3-[1-piperazino)propyl]-phthalazin-1(2H)-one and pharmaceutically acceptable salts thereof.

14. Trans-6-[2-[4-(methylthio)phenyl]ethenyl]-2-[3-(dimethylamino)propyl]phthalazin-1(2H)-one and pharmaceutically acceptable salts thereof.

* * * * *

UNITED STATES PATENT AND TRADEMARK OFFICE
CERTIFICATE OF CORRECTION

PATENT NO. : 4,769,369
DATED : September 6, 1988
INVENTOR(S) : T. L. Thomas, L. A. Radov It is certified that error appears in the above—identified patent and that said Letters Patent is hereby corrected as shown below:

In claim 11: Insert

"$C_1$-$C_4$ alkoxy or" after the term "hydroxyl", and before the term "$C_1$-$C_4$ alkylthio".

Signed and Sealed this

Seventeenth Day of January, 1989

Attest:

DONALD J. QUIGG

Attesting Officer

Commissioner of Patents and Trademarks